United States Patent
Courtney

[19]
[11] Patent Number: 5,945,406
[45] Date of Patent: Aug. 31, 1999

[54] THERAPEUTIC COMPOUNDS WITH PYRIMIDINE BASE

[75] Inventor: Stephen Martin Courtney, Marcham, Oxon, United Kingdom

[73] Assignee: Oxford Glycosciences (UK) Ltd., Abingdon, United Kingdom

[21] Appl. No.: 08/997,309

[22] Filed: Dec. 23, 1997

Related U.S. Application Data

[63] Continuation-in-part of application No. PCT/GB96/01519, Jun. 24, 1996, abandoned
[60] Provisional application No. 60/016,762, May 3, 1996, and provisional application No. 60/016,973, May 7, 1996.

[30] Foreign Application Priority Data

| Jun. 23, 1995 | [GB] | United Kingdom | 9512868 |
| Apr. 23, 1996 | [GB] | United Kingdom | 9608372 |
| Apr. 25, 1996 | [GB] | United Kingdom | 9608547 |

[51] Int. Cl.$^6$ .................................................. A61K 31/715
[52] U.S. Cl. .......................... 514/32; 514/274; 536/17.3; 536/17.4; 544/309; 544/311; 544/316; 544/313; 544/318; 544/319
[58] Field of Search .................... 514/32, 274; 536/17.3, 536/17.4; 544/309, 311, 313, 318, 319

[56] References Cited

U.S. PATENT DOCUMENTS

| 3,354,160 | 11/1967 | Duchinsky et al. ..................... 260/251 |
| 4,248,999 | 2/1981 | Baba et al. . | |

FOREIGN PATENT DOCUMENTS

| 0 119 650 | 9/1984 | European Pat. Off. . |
| 0 119 650 A2 | 9/1984 | European Pat. Off. . |
| 55-153796 | 11/1980 | Japan . |
| 58029798 | 2/1983 | Japan . |
| 58-72599 | 4/1983 | Japan . |
| 2-295997 | 12/1990 | Japan . |
| 5-17494 | 1/1993 | Japan . |
| 5017494 | 1/1993 | Japan . |
| 6610360 | 1/1967 | Netherlands . |
| 1 541 185 | 2/1979 | United Kingdom . |
| 9700882 | 1/1997 | WIPO . |
| 9828318 | 7/1998 | WIPO . |

OTHER PUBLICATIONS

Al–Masoudi et al, Synthesis and reactions of some uracil and 5–halouracil nucleosides of 2–acetamido–2–deoxy–D–glucose. Acta Chem. Scand. 51(9), 958–962, 1997.

Sun et al. Synthesis of N–glucuronides of 5–fluorouracil and their antitumor activities. Chin. Chem. Lett. 5(5), 375–376, 1994.

Chouini–Lalanne et al. Synthesis of glucuronides of fluoropyrimidine drugs: N– and O–glucuronides of 5–fluorcytosine and 5–fluorouracil. Nucleosides Nucleotides. 12(3–4), 331–350, 1993.

Germane et al. A comparison of the antitumor activity and neurotropic properties of 5–fluorouracil, ftorafur, and 5–fluorouracil–N–glucuronide. Eksp. Klin. Farmakoter. 16, 36–44, 1987.

Kulinkovich et al. Synthesis of 5–fluorouracil nucleosides of D–glucopyanuronic acid. Zh. Obshch. Khim. 53(7), 1649–1651, 1983.

Baba et al., 1978, "5–Fluorouracil O–β–D–Glucuronide As a Newly Synthesized Chemically Modified, Nontoxic Anticancer Drug", Gann 69:283–284.

Biessen et al., 1995, "Synthesis of Cluster Galactosides with High Affinity for the Hepatic Asialoglycoprotein Receptor", J. Med. Chem. 38:1538–1546.

(List continued on next page.)

*Primary Examiner*—Thurman K. Page
*Attorney, Agent, or Firm*—Pennie & Edmonds LLP

[57] ABSTRACT

Compounds of formula (I):

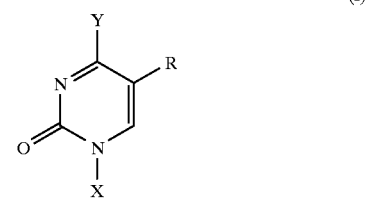

wherein:
R is halogen;
Y is hydrogen, $NH_2$, SH or OH;
X is:

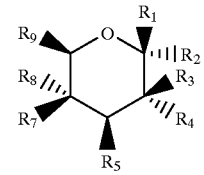

wherein:
either $R_1$ or $R_2$ is a bond, with the other being hydrogen;
either $R_3$ or $R_4$ is hydrogen, with the other being hydrogen, OH, OAc or NHAc;
$R_5$ is OH or OAc;
either $R_7$ or $R_8$ is hydrogen, with the other being OH or OAc;
$R_9$ is hydrogen, $CH_2OH$ or $CH_2OAc$;
with the proviso that when $R_4$ is OH, OAc or NHAc then $R_8$ is hydrogen;
and enantiomers of such compounds, are disclosed. Pharmaceutical formulations comprising such compounds, their use in the treatment of various disease states, and methods of treatment employing the compounds are also provided.

20 Claims, No Drawings

OTHER PUBLICATIONS

Cheng and Ollapally, 1976, "A Facile Alternative Synthesis of 1–(β–D–Xylopyranosyl) Uracil and its 5–Bromo Derivative", J. Carbohydates, Nucleosides, Nucleotides 3:229–234.

Efange et al., 1985, "Synthesis and Biological Activities of 2–Pyrimidinone Nucleosides. 2. 5–Halo–2–pyrimidinone 2'–Deoxribonucleosides", J. Med. Chem. 28:904–910.

Etzold and Langen, 1965, "Pyrimidine Nucleosides of 2–Deoxy–D–Glucose", Chem. Ber. 98:1988–1997 (and certified English translation thereof).

Herdewijn et al., 1991, "Synthesis of 2'–Deoxy–2'–Fluoro–D–Arabinopyranosyl Nucleosides and Their 3', 4'–Seco Analogues", Nucleosides & Nucleotides 10:1525–1549.

Kaneko et al., 1977, "Synthesis of O–Glycosidic Derivatives of 5–Fluorouracil and Their Antitumour Activities", Nucl. Acids. Res., Spec. Pub. No. 3:s35–s38.

Krebs et al., 1994, "Binding of D–Galactose–Terminated Ligands to Rabbit Asialoglycoprotein Receptor", Carbohydrate Res. 254:257–268.

Lee, 1991, "Ligand Structural Requirements for Recognition and Binding by the Hepatic Asialoglycoprotein Receptor", In: *Liver Diseases, Targeted Diagnosis and Therapy Using Specific Receptors and Ligands* (Wu & Wu, eds.) pp. 65–85.

Lee, 1992, "Biochemistry of Carbohydrate–Protein Interaction", FASEB J. 6:3193–3200.

Lee and Lee, 1987, Preparation of Cluster Glycosides of N–Acetylgalactosamine that Have Subnanomolar Binding Constants Towards the Mammalian Hepatic Gal/GalNAc––Specific Receptor, Glycoconjugate 317–328.

Ogura et al. 1991, "A Stereo–Controlled Nucleoside Synthesis from Anhydro Sugars", Nucleic Acid Chem. 4:109–112.

Ohya et al., 1991, "Preparation of Albumin Microspheres Grafted Galactose Residues Through Polyethylene–Glycol Spacers, Release Behavior of 5–Fluorouracil From Them, and Their Lectin–Mediated Aggregation", J. Macromol. Sci.– Chem. A28:743–760.

Ozaki et al., 1995, "The Differences in Structural Specificity for Recognition and Binding Between Asialoglycoprotein Receptors of Liver and Macrophages", Glycoconjugate J. 12:268–274.

Perigaud et al., 1992, "Nucleoside Analogues As Chemotherapeutic Agents: A Review", Nucleosides & Nucleotides 11:903–945.

Quelo et al., 1972, "Anomerization and Isomerization of 2'–Deoxyuridine by Means of Derivatives Resulting From Saturation of the 5,6 Double Bond of the Pyrimidic Cycle", C.R. Acad. Sc. Paris 275:1137–1140 (and certified English translation thereof).

Saneyoshi et al., 1978, "Synthetic Nucleosides and Nucleotides. XI. Facile Synthesis and Antitumor Activities of Various 5–Fluoropyrimidine Nucleosides", Chem. Pharm. Bull. 26:2990–2997.

Schwarz et al., 1980, "Preparation, Antibacterial Effects and Enzymatic Degradation of 5–Fluorouracil Nucleosides", Collection Czechoslov. Chem. Commun. 45:3217–3229.

Seymour, 1994, "Soluble Polymers for Lectin–Mediated Drug Targeting", Adv. Drug Delivery Rev. 14:89–111.

Sun et al., 1992, "Synthesis of β–D–Galactopyranosides of 5–Fluorouracil", Youji Huaxue 12:273–277 (and certified English translation thereof).

Van der Sluijs and Meijer, 1991, "Limitations on the Specificity of Targeting Asialoglycoprotein–Drug Conjugates to Hepatocytes", In: *Liver Diseases, Targeted Diagnosis and Therapy Using Specific Receptors and Ligands* (Wu & Wu, eds.) pp. 235–264.

Vorbruggen and Bennua, 1978, "New Simplified Nucleoside Synthesis", Tetrahedron Letters 15:1339–1342.

Wadhwa and Rice, 1995, "Receptor Mediated Glycotargeting", J. Drug Targeting 3:111–127.

Zhong et al., 1995, "Preparation of Galactosyl–Interferon–$\alpha_1$ and its Hepatic Targeting Property", Chinese J. Med. Chem. 5:164–168 (and certified English translation thereof).

Henin et al., 1991, "Lipophilic Glycosyl Phosphotriester Derivatives of AZT: Synthesis, NMR Transmembrane Transport Study, and Antiviral Activity", J. Med. Chem. 34: 1830–1837.

THERAPEUTIC COMPOUNDS WITH PYRIMIDINE BASE

This is a continuation-in-part of International Application No. PCT/GB96/01519, filed Jun. 24, 1996 (now abandoned) and claims the benefit of U.S. provisional applications No. 60/016,762, filed May 3, 1996, and 60/016,973, filed May 7, 1996, each of which is incorporated herein by reference in its entirety.

The present invention relates to novel pyrimidin compounds, pharmaceutical formulations comprising such compounds and their use in medical treatment, particularly the treatment of cancer and infections by pathogens.

Pyrimidin bases are a vital component of many currently used therapeutic products e.g. 5-fluorouracil and 5-flucytosine. 5-Fluorouracil (5-FU) was introduced as a rationally synthesised anti-cancer agent more than 30 years ago and is still widely used in the treatment of many cancers (Duschinsky, et al, J. Am. Chem. Soc.,79: 4559 (1957); Heidelberger, et al, Nature, 179: 663 (1957)). The utility of 5-FU is however low due to toxic side effects, a common problem with anti-cancer agents.

A number of derivatives of 5-FU have been synthesised over the years, which are either active metabolites (Heidelberger, Cancer Research, 30: 1549 (1970); Burchenal, et al, Ann. NY. Acad. Sci, 255: 202 (1975); Saneyoshi, et al, Chem. Pharm. Bull., 26 (10): 2990 (1978)) or simple prodrugs which act as repository forms of 5-FU (Holshouser, et al, J. Med. Chem., 28: 242 (1985); Hiller, et al, Dokl. Akad. Nauk. USSR, 176: 332 (1967);Ueda, et al, Chem. Pharm. Bull., 30, (1): 125 (1982)). Some of these compounds provide less toxic alternatives to 5-FU and have found a place in clinical practice. However these less toxic compounds are none the less widely taken up by many different tissue types and consequently still display significant adverse, dose related side effects. Thus, it has been a long-term goal of the pharmaceutical industry to improve safety and efficacy of such therapeutic agents by improving tissue selectivity and tissue targeting.

Many drug-design approaches have been taken toward this end. One broad class of such targeted drugs has relied on obtaining specific delivery by complexing cell-binding proteins or macromolecules with therapeutic agents. For example, a wide variety of reports have described the preparation of drugs conjugated with cell-targeted monoclonal antibodies, protein/liposome aggregates or viruses. An alternate approach for targeted drug delivery employs the fact that many cells themselves possess unique binding receptors on their surfaces. Thus, targeted therapeutic agents may be designed to incorporate ligand molecules which can be bound by these cell-specific receptors.

Carbohydrate binding proteins represent one important class of cell-surface receptors that pharmaceutical scientists have designed drugs to target. The first cell-surface carbohydrate binding protein was characterized about twenty years ago (Ashwell and Morell, Adv. Enzymol. Relat. Areas Mol. Biol. 41: 99–128 (1974); Pricer, and Ashwell, J. Biol. Chem., 246: 4825–4833 (1971)). These researchers showed that glycoproteins treated to remove terminal sialic acids on attached oligosaccharides were specifically taken up by liver cells when injected into animals (Ashwell and Morell, Adv. Enzymol. Relat. Areas Mol. Biol. 41: 99–128 (1974)). Subsequent work demonstrated that this liver-specific ligand retention is mediated by a carbohydrate-recognizing receptor, now commonly referred to as the asialoglycoprotein receptor, that occurs on the surface of hepatocytes (Lodish, Trends Biochem. Sci., 16: 374–377 (1991); Weiss and Ashwell, Prog. Clin. Biol. Res. 300: 169–184 (1989)).

More recently, other carbohydrate receptors have also been characterized. For example, mannose/N-acetylglucosamine and fucose receptors are found on cells such as macrophages and monocytes (Haltiwanger and Hill, J. Biol. Chem. 261: 7440–7444 (1986); Ezekowitz and Stahl, J. Cell Sci. Suppl. 9: 121–133 (1988); Haltiwanger, et al, J. Biol. Chem. 261: 7433–7439 (1986)). Selectin receptors, carbohydrate-binding proteins specific for Lewis or sialyl-Lewis blood group oligosaccharide structures, occur on endothelial cells, neutrophils and platelets (Munro, Eur. Heart. J. 14 suppl K: 72–77 (1993)).

In addition to their particular carbohydrate specificity, these carbohydrate binding proteins can be further classified by whether or not they participate in receptor mediated endocytosis. Receptors which do not mediate endocytosis remain on the cell surface, with or without bound ligands, for comparatively long time periods, while receptors mediating endocytosis are rapidly internalized from the cell-surface via clatherin coated pits, delivering bound ligands to endocytic vesicles which in turn quickly merge with lysosomes (Trowbridge, Curr. Opin. Cell Biol. 3: 634–641 (1991); Schwartz, Targeted. Diagn. Ther. 4: 3–39 (1991); Stoorvogel, et al, Cell, 65: 417–427 (1991); DeCourcy and Storrie, Exp. Cell Res., 192: 52–60 (1991); Haylett and Thilo, J. Biol. Chem., 266: 8322–8327 (1991)). The asialoglycoprotein and mannose/N-acetylglucosamine receptors described above mediate endocytosis, whereas current evidence indicates the selectin receptors do not (Dini, et al, Biol. Cell, 74: 217–224 (1992); Munro, Eur. Heart. J. 14 suppl K: 72–77 (1993)).

Many reports have described the design of therapeutic agents conjugated with carbohydrates to target receptors mediating endocytosis on specific cells. Adding glycolipids to liposomes can greatly improve the targeting of these large aggregates to specific cells (Mumtaz, et al, Glycobiology, 1: 505–510 (1991); Barratt, et al Biochim. Biophys. Acta 862: 153–164 (1986)). Drugs and carbohydrates have been combined on dextran scaffolds for targeting, as with AraC-dextran-galactose complexes used to deliver drugs to liver cells. Similarly, carbohydrate-modified chitosan microspheres improves the cell targeting of encapsulated therapeutic agents to some cell types (Ohya, et al, J. Microencapsul. 10: 1–9 (1993)). Antimony complexes with yeast mannan derivatives provide a therapy for Leishmania-infected macrophages (Cantos, et al, Biochem. J., 289: 155–160 (1993)).

Poly-lysine is employed in a range of drug designs as a scaffold for the combination of therapeutic agents and carbohydrates. For example, poly-lysine-based complexes are used for applications ranging from the targeting of DNA carriers for gene therapy (Wu, et al, J. Biol. Chem., 269: 11542–11546s (1994); McKee, et al, Bioconjug. Chem. 5: 306–311 (1994); Midoux, et al, Nucleic Acids Res. 21: 871–878 (1993)) to the selective delivery of anti-viral agents to liver cells (Fiume, et al, FEBS Lett 203: 203–206 (1986)).

Finally a wide variety of glycoproteins (native, as well as ones modified to manipulate the attached carbohydrate structures), neoglycoproteins, and glycopeptides have been coupled to therapeutic agents to improve their cell targeting characteristics (Fiume, et al, Biochem. Pharmacol. 47: 643–650 (1994); Cristiano, et al, Proc. Natl. Acad. Sci. U.S.A. 90: 11548–11552 (1993); Sett, et al, J. Infect. Dis., 168: 994–999 (1993); Fiume, et al, Crit. Rev. Ther. Drug Carrier Syst. 4: 265–284 (1988); Bonfils, et al, Nucleic Acids Res., 20: 4621–4629 (1992); Steer and Ashwell, Prog. Liver Dis. 8: 99–123 (1986); Grabowski, et al, Ann. Inter. Med. 122: 33–39 (1995); Bonfils, et al, Bioconj. Chem. 3: 277–284 (1992)).

Another class of binding proteins of possible importance to the field of targeted therapeutics are the plasma membrane carbohydrate transporters. These proteins bind carbohydrates, usually monosaccharides, present in the fluids around the cell and transfer them directly into the cell's cytoplasm (Bell, et al, J. Biol. Chem., 268: 19161–19164 (1993); Gould and Holman, Biochem. J. 295: 329–341 (1993)). For example, one or more types of glucose transporters occur on the surfaces of all cells (Marrall, et al, Cell Signal. 5: 667–675 (1993); Pardridge, Ann. N. Y. Acad. Sci. 27, 692: 126–137 (1993); Gould and Holman, Biochem. J. 295: 329–341 (1993); Pardridge, Adv. Exp. Med. Biol. 291: 43–53 (1991); Mueckler, Eur. J. Biochem. 219: 713–725 (1994); Yang and Holman, J. Biol. Chem. 268: 4600–4603 (1993)).

More recently there has been a suggestion that it may be possible to enhance the uptake of carbohydrate containing neuropeptides through interaction with monosaccharide transporters in the endothelium of the blood brain barrier. (Polt, et al, Proc. Natl. Acad. Sci. U.S.A., 91: 7114–7118 (1994)).

Several drug-conjugates utilising carbohydrate mediated targeting have been investigated over the past few years (Monsigny, et al, Ann. NY. Acad. Sci., 551: 399 (1988); Monsigny, et al, Advanced Drug Delivery Reviews, 14: 1–24 (1994)). Previous work has involved macromolecular carriers incorporating sugar moieties, such as neoglycoproteins (Sett, et al, J. Infect. Dis., 168: 994 (1993); Trouet, et al, "Targeting of Drugs," eds. G. Gregoriadis, J. Senior and A. Trouet, Plenum, NY, Vol. 47 (1981); Molema, et al, J. Med. Chem., 34: 1137 (1991); Graham, et al, Bioconjugate Chem., 5 (6): 547 (1994); Fiume, et al, FEBS LETTS., 116 (2): 185 (1980); Enriquez, et al, WO 94/2248; Josephson, et al, U.S. Pat. No. 5,336,506; Jung, et al, WO 93/252339; Josephson, et al, WO 92/17216; Josephson, et al, WO 92/11037; Menz, et al, WO 90/01295; Bijsterbosch and Van Berkel, Molecular Pharmacology, 41: 404 (1991)) and glycosylated polymers (Nishikawa, et al, Pharmaceutical Research, 10 (9): 1253 (1993); Kobayashi and Sumitomo, J. Macromol. Sci-Chem., A25(5–7): 655 (1988)). Despite some success, particularly for the targeting to the asialoglycoprotein receptor via complexes of galactose containing residues and for targeting to macrophages via complexes of mannose containing residues, these attempts so far have not resulted in a therapeutically viable product. These previous approaches to targeting have concentrated on the targeting of large, complex ligands incorporating complex carbohydrate moieties associated with the targeted pharmacophore. The main problems associated with these products relate to their complex nature, cost, immunogenicity, difficulty in conjugation and, in some cases, undesirable specific tissue interaction of the carrier proteins.

As a result the targeting strategies proposed to date have not in fact been practical.

The belief that such ligand complexity is required in order to achieve targeting has in fact led away from a consideration of an approach utilising simpler carbohydrate moieties and associated chemistry to achieve targeting of therapeutically useful compounds. The use of simpler carbohydrate ligands has been previously discounted on the grounds that carbohydrate binding receptors have evolved in nature to recognise complex carbohydrate molecules and will therefore exhibit poor binding with simpler sugars. However, such an approach might be expected to involve less complex synthesis and therefore lower cost as well as producing less potentially immunogenic compounds.

We have now developed a simple, efficient method of targeting pyrimidin-based therapeutics to sugar-specific binding proteins. Conjugation of the carbohydrate to the pyrimidin takes place via a simple chemical process. The sugars used are monosaccharides or other simple, low molecular weight carbohydrates. The resulting glycoconjugates are metabolised in target tissues to generate cytotoxic species capable of destroying infectious organisms or tumour cells localised therein. However, the glycoconjugates themselves have low intrinsic toxicity and therefore can deliver the therapeutic benefit of pyrimidines without their toxic side effects. Thus, in a first aspect, the invention provides a compound of formula (I):

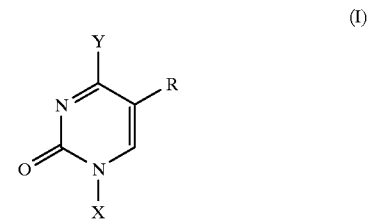

wherein:
R is halogen;
Y is hydrogen, $NH_2$, SH or OH;
X is:

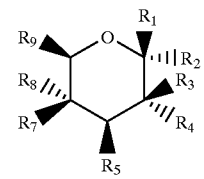

wherein:
either $R_1$ or $R_2$ is a bond, with the other being hydrogen;
either $R_3$ or $R_4$ is hydrogen, with the other being hydrogen, OH, OAc or NHAc;
$R_5$ is OH or OAc;
either $R_7$ or $R_8$ is hydrogen, with the other being OH or OAc;
$R_9$ is hydrogen, $CH_2OH$ or $CH_2OAc$;
with the proviso that when $R_4$ is OH, OAc or NHAc then $R_8$ is hydrogen;
and enantiomers of such compounds.

The skilled reader will appreciate that formula I represents compounds which can be classified as either α or β anomers. Thus, both α and β anomers are included within the scope of the invention.

In addition, formula I will embody both D and L enantiomers and thus, both D and L enantiomers fall within the scope of the present invention.

By "halogen" is meant fluoro, chloro, bromo or iodo.

In one preferred embodiment the invention provides a compound of the formula (I) wherein:
R is fluoro;
Y is OH; and
$R_1$ and $R_2$ are as defined in formula I;
either $R_3$ or $R_4$ is hydrogen with the other being OH;
$R_5$ is OH;
either $R_7$ or $R_8$ is hydrogen with the other being OH;
$R_9$ is hydrogen or $CH_2OH$.

Preferred compounds falling within the scope of this embodiment include:

1-β-D-Galactopyranosyl-5-fluorouracil;
1-α-D-Galactopyranosyl-5-fluorouracil;
1-(β-D-2-Deoxyglucopyranosyl)-5-fluorouracil;
1-(α-D-2-Deoxyglucopyranosyl)-5-fluorouracil;
1-α-D-Mannopyranosyl-5-fluorouracil;
1-(β-D-2-Deoxy-2-N-acetylgalactopyranosyl)-5-fluorouracil;
1-(β-D-2-Deoxygalactopyranosyl)-5-fluorouracil;
1-(α-D-2-Deoxygalactopyranosyl)-5-fluorouracil;
1-β-L-Arabinopyranosyl-5-fluorouracil;
1-α-L-Arabinopyranosyl-5-fluorouracil;
1-β-L-Galactopyranosyl-5-fluorouracil;
1-α-L-Galactopyranosyl-5-fluorouracil;
1-(β-D-2-O-Acetylgalactopyranosyl)-5-fluorouracil;
1-(β-D-2,6-Di-O-Acetylgalactopyranosyl)-5-fluorouracil; and
1-(β-D-2-deoxy-2-N-acetyl-6-O-acetylgalactopyranosyl)-5-fluorouracil.

Particularly preferred compounds within this embodiment include:
1-β-D-Galactopyranosyl-5-fluorouracil;
1-β-L-Galactopyranosyl-5-fluorouracil;
1-(β-D-2-Deoxy-2-N-acetylgalactopyranosyl)-5-fluorouracil; and
1-β-L-Arabinopyranosyl-5-fluorouracil,
with 1-β-D-Galactopyranosyl-5-fluorouracil, 1-β-L-Galactopyranosyl-5-fluorouracil and 1-(β-D-2-Deoxy-2-N-acetylgalactopyranosyl)-5-fluorouracil being most preferred.

In a second preferred embodiment the invention provides compounds wherein:
R is fluoro;
Y is $NH_2$;
$R_1$ and $R_2$ are as defined in formula I;
either $R_3$ or $R_4$ is hydrogen with the other being OH;
$R_5$ is OH;
either $R_7$ or $R_8$ is hydrogen with the other being OH;
$R_9$ is hydrogen or $CH_2OH$.

Preferred compounds which fall within the scope of this embodiment of the invention include:
1-β-D-Galactopyranosyl-5-fluorocytosine;
1-(β-D-2-Deoxyglucopyranosyl)-5-fluorocytosine;
1-α-D-Mannopyranosyl-5-fluorocytosine;
1-(β-D-2-Deoxy-2-N-acetylgalactopyranosyl)-5-fluorocytosine;
1-(β-D-2-Deoxygalactopyranosyl)-5-fluorocytosine;
1-β-L-Arabinopyranosyl-5-fluorocytosine;
1-α-D-Lyxopyranosyl-5-fluorocytosine; and
1-β-D-Arabinopyranosyl-5-fluorocytosine.

Particularly preferred compounds within this embodiment of the invention include:
1-β-D-Galactopyranosyl-5-fluorocytosine;
1-(β-D-2-Deoxyglucopyranosyl)-5-fluorocytosine; and
1-(β-D-2-Deoxygalactopyranosyl)-5-fluorocytosine.

The use of the compounds of the invention forms a second aspect of the invention.

Compounds of general formula (I) may be prepared by any suitable method known in the art and/or by the processes described below.

Thus, according to a third aspect of the invention there is provided a process for preparing a compound of general formula (I), as defined above, the process comprising:

(a) treating a compound of general formula (III):

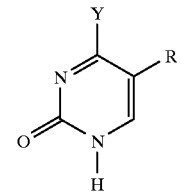

(III)

with a carbohydrate derivative of general formula (IV):

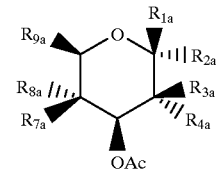

(IV)

wherein $R_{1a}$ or $R_{2a}$ independently represents either hydrogen or any suitable donor group eg. halogen, OAc or SMe; either $R_{3a}$ or $R_{4a}$ is hydrogen with the other being hydrogen, OAc or NHAc; either $R_{7a}$ or $R_{8a}$ is hydrogen with the other being OAc; and $R_{9a}$ is hydrogen or $CH_2OAc$, in the presence of a silylating reagent eg. hexamethyldisilazane and trimethylsilyl chloride, and a catalyst eg. $CF_3SO_3H$, $NaBF_4$, $SnCl_4$, $ZnCl_2$, $TiCl_4$, TmsOTf, $BF_3.Et_2O$ optionally followed by conversion of one or more OAc groups to OH groups;

(b) reacting a compound of formula (V):

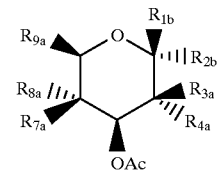

(V)

wherein $R_{1b}$ and $R_{2b}$ are either $NHCONH_2$ or hydrogen, and $R_{3a}$, $R_{4a}$, $R_{7a}$, $R_{8a}$, and $R_{9a}$ are as defined in formula (IV), with a compound of formula (VI) or (VII):

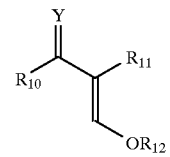

(VI)

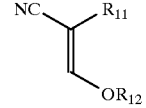

(VII)

wherein Y represents O or S, $R_{10}$ represents alkoxy $R_{11}$ represents halogen and $R_{12}$ represents hydrogen, alkyl, Na or K, in the presence of a base eg. sodium methoxide.

Compounds of formula (V) wherein $R_{1b}$ and $R_{2b}$ are either $NHCONH_2$ or hydrogen can be produced by treating a compound of general formula (V), wherein $R_{1b}$ or $R_{2b}$ independently represents either hydrogen or NH2 and $R_{3a}$, $R_{4a}$, $R_{7a}$, $R_{8a}$ and $R_{9a}$ are as defined in general formula (IV) above, with a carboxylation reagent eg. ethyl chloroformate, 1,1-carbonyl diimidazole, followed by treatment with ammonia.

Compounds of general formula (VI) or (VII) may be prepared from the appropriate acetate derivative (VIII) or nitrile derivative (IX):

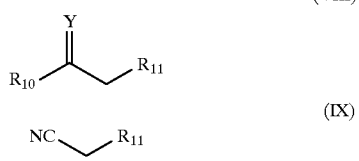

respectively, by reaction with methyl formate and a base eg. potassium methoxide wherein Y, $R_{10}$ and $R_{11}$ are as defined above; or (c) treating a compound of general formula (X):

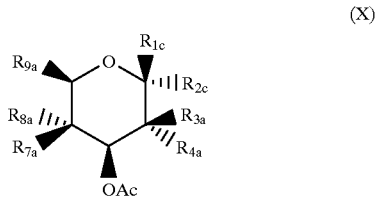

wherein $R_{1c}$ or $R_{2c}$ is $NH_2$ with the other being hydrogen and $R_{3a}$, $R_{4a}$, $R_{7a}$, $R_{8a}$ and $R_{9a}$ are as defined in general formula (V), with a compound of general formula (XI):

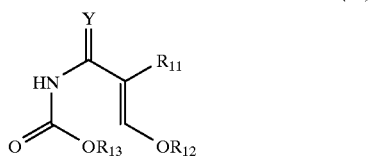

wherein $R_{13}$ represents an alkyl group, and $R_{11}$ and $R_{12}$ are as defined above, optionally followed by conversion of one or more OAc groups to OH groups.

Compounds of general formula (XI) may be prepared from reaction of the appropriately substituted acetic acid derivative (XII):

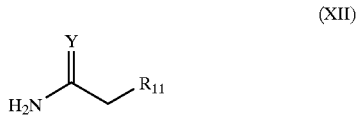

with an alkyl chloroformate followed by reaction with methyl formate in the presence of base eg. sodium methoxide, wherein Y and $R_2$ are as defined above.

Compounds of formula (VII) may be prepared by methods known in the art (e.g. J. Truce, J. Amer. Chem. Soc.,70: 2828 (1948)).

A compound of general formula (I) may be transformed into another compound of general formula (I) using methods well known to those skilled in the art.

Compounds of general formula (I) wherein X represents hydrogen may be available through the usual sources, however they may be prepared via a number of common procedures, (e.g.) such as the reaction of urea with compounds of general formula (VI) or (VII) as defined above; in the presence of a base eg. sodium methoxide in ethanol.

Furthermore compounds of general formula (I) wherein R represents halogen, may be produced by transformation of compounds wherein R is hydrogen by reaction with an appropriate halogenation reagent eg. flourination with trifluoromethylhypofluorite and triethylamine. (e.g. M. J. Robbins and S. R. Naik, J. Amer. Chem. Soc., 93: 5272 (1971)).

Compounds of general formula (I) wherein Y represents SH may be prepared by reaction of the appropriate compound wherein Y represents OH with common procedures known in the art eg. Lawesson's reagent (2,4-bis(4-methoxyphenyl)-1,3,2,4-dithiadiphosphetane-2,4-disulphide), $P_4S_{10}$ or bis(tricyclohexyltin) sulphide.

The skilled man will appreciate that by altering, for example, the solvent and/or catalyst in reactions as described above the ratio of α:β anomers can be varied. Alternatively, α anomers can be obtained in a higher ratio utilising the mannose configuration at position 2 followed by epimerisation (see for example R. U. Lemieux and A. R. Morgan, Can. J. Chem., 43: 2190 (1965)).

The methodology utilised in this invention is based upon the published procedure of Vorbruggen and Bennua (Vorbruggen and Bennua, Tet. Lett., 1339, (1978)) for the synthesis of nucleosides.

According to a fourth aspect the present invention provides pharmaceutical formulations comprising one or more compounds of the invention, together with one or more pharmaceutically acceptable carriers or excipients.

Pharmaceutical formulations may be presented in unit dose forms containing a predetermined amount of active ingredient per dose. Such a unit may contain for example 50 mg/kg to 600 mg/kg, preferably 50 mg/kg to 300 mg/kg and more preferably 50 mg/kg to 150 mg/kg depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For infections of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The compounds of the present invention are useful in that they are capable of targeting, allowing delivery of therapeutic agents to a desired location. Thus, the compounds of the invention can be used in the treatment or prophylaxis of various conditions, including cancer, including metastatic liver cancer, fungal infections, etc., depending on which therapeutic agent is being targeted.

In addition aspects, therefore, the present invention provides:

(i) the use of a compound of the invention in the manufacture of a medicament for the treatment of cancer;

(ii) the use of a compound of the invention in the manufacture of a medicament for the treatment of a fungal infection;

(iii) a method for the treatment of cancer, particularly liver cancer, which comprises the step of administering to a patient an effective amount of a compound of the invention;

(iv) a method for the prophylaxis or treatment of metastatic liver cancer which comprises the step of administering to a patient an effective amount of a compound of the invention;

(v) a method for the treatment of a fungal infection which comprises the step of administering to a patient an effective amount of a compound of the invention;

(vi) the use of a compound of the invention in the manufacture of a medicament for use in the prophylaxis or treatment of psoriasis;

(vii) a method for the prophylaxis or treatment of psoriases which comprises the step of administering to a patient an effective amount of a compound of the invention;

(viii) the use of a compound of the invention in the manufacture of a medicament to prevent cell division; and (ix) a method of preventing cell division which comprises administering to a subject an effective amount of a compound of the invention.

The invention will now be described with reference to the following examples, which are not intended to limit the scope of the invention in any way.

Preferred features of each aspect of the invention are as for each other aspect mutatis mutandis.

EXAMPLE 1

1-β-D-Galactopyranosyl-5-fluorouracil and 1-α-D-Galactopyranosyl-5-fluorouracil

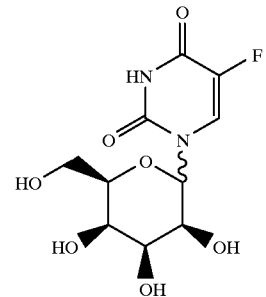

A mixture of 5-fluorouracil (0.2 g, 1.54 mmol) and peracetylated galactose (0.53 g, 1.54 mmol) was stirred in acetonitrile (25 ml) at 0° C., under argon. Hexamethyldisilizane (0.26 ml, 1.23 mmol) was added followed by trimethylsilyl chloride (0.16 ml, 1.23 mmol) and the mixture stirred for 30 min. A solution of tin(IV) chloride (0.22 ml, 1.84 mmol) in acetonitrile (5 ml) was added dropwise and after stirring at 0° C. for 30 min the solution was stirred at room temperature or heated at ~70° C. until no starting material remained. The reaction mixture was diluted with ethyl acetate (50 ml) and washed succesively with sat. sodium bicarbonate solution (40 ml), water (40 ml) and brine (40 ml). The organic layer was dried and evaporated under reduced pressure and the crude product purified by flash chromatography (5% MeOH/DCM) to give colourless crystals (0.5 g, 71%).

A sample of the above product (0.10 g) was dissolved in methanol and a sodium methoxide solution added (1M in MeOH; ~10 drops). After stirring at rt for 2 h the reaction was neutralised with Dowex H⁺ resin, filtered and evaporated under reduced pressure. The product was obtained as a mixture of the α and β anomers. These may be separated by the usual methods, for example, HPLC or column chromatography.

Anal. Calc. for $C_{10}H_{13}FN_2O_7$ (+0.5$H_2O$) Requires C 39.87 H 4.65 N 9.30 Found C 39.61 H 4.98 N 8.57

$^1$H NMR (β-anomer): δ3.8–4.0 (5H, m, CH, CH2), 4.1 (1H, d, CH), 5.62 (1H, d, CH), 8.15 (1H, d, =CH)

$^1$H NMR (α-anomer): δ3.7–3.8(3H, m, CH, CH2), 4.3–4.35(1H, m, CH), 4.35–4.4 (1H, m, CH), 4.42–4.45 (1H, m, CH), 5.90(1H, dd, CH), 8.0 (1H, d, =CH).

EXAMPLE 2

1-β-L-Galactopyranosyl-5-fluorouracil and 1-α-L-Galactopyranosyl-5-fluorouracil

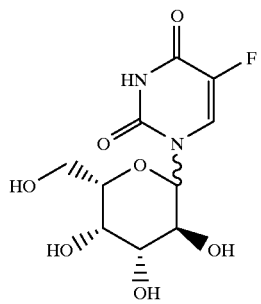

The above compound was prepared using the method described in Example 1, using peracetylated L-galactose as the starting material. The product was obtained as a mixture of the α and β anomers. These may be separated by the usual methods, for example, HPLC, column chromatography.

Mp. 145–148° C.

Anal. Calc. for $C_{10}H_{13}FN_2O_7$ (+$H_2O$) Requires C 38.71 H 4.84 N 9.03 Found C 39.19 H 4.89 N 8.66

$^1$H NMR (β-anomer): δ3.8–4.0 (5H, m, CH, CH2), 4.1 (1H, m, CH), 5.6–5.62(1H, d, CH), 8.1 (1H, d, =CH)

$^1$H NMR (β-anomer): δ3.55–3.65 (3H, m, CH, CH2), 4.15–4.2 (1H, m, CH), 4.2–4.22 (1H, m, CH), 4.25–4.3(1H, m, CH), 5.72 (1H, dd, CH), 7.85 (1H, d, =CH).

EXAMPLE 3

1-(β-D-2-Deoxyglucopyranosyl)-5-fluorouracil and 1-(α-D-2-Deoxyglucopyranosyl)-5-fluorouracil

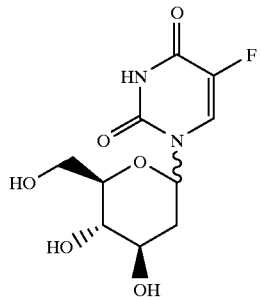

The above compound was prepared using the method described in Example 1, using peracetylated 2-deoxyglucose as the starting material. This gave a colourless product (87% yield for the second step).

The product was obtained as a mixture of the α and β anomers. These may be separated by the usual methods, for example, HPLC, column chromatography.

Mp. 125–130° C.

Anal. Calc. for $C_{10}H_{13}FN_2O_6$ (+0.5$H_2O$) Requires C 42.10 H 4.91 N 9.82 Found C 42.07 H 4.85 N 9.70

$^1$H NMR (β-anomer): δ1.85–1.9 (1H, m, CH), 2.35 (1H, m, CH), 3.45 (1H, m, CH), 3.82 (1H, m, CH), 3.9–4.0 (2H, m, CH₂), 5.82 (1H, d, CH), 8.05 (1H, d, =CH).

$^1$H NMR (α-anomer): δ2.1–2.19 (1H, m, CH), 2.25–2.3 (1H, m, CH), 3.8–4.0 (1H, m, CH), 4.15–4.2 (1H, m, CH), 6.10 (1H, dd, CH), 8.05 (1H, d, =CH).

EXAMPLE 4

1-α-D-Mannopyranosyl-5-fluorouracil

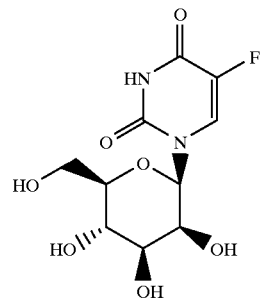

The above compound was prepared using the method described in Example 1, using peracetylated mannose as the starting material. This gave a colourless product (58% yield for the second step).

Mp. 120–125° C.

Anal. Calc. for $C_{10}H_{13}FN_2O_7$ (+0.5$H_2O$) Requires C 39.87 H 4.65 N 9.30 Found C 40.25 H 4.62 N 9.24

$^1$H NMR: δ3.88 (1H, dd, CH), 3.99 (1H, m, CH), 4.15 (1H, m, CH), 4.2–4.3 (3H, m, CH, CH₂), 6.02 (1H, d, CH), 8.1 (1H, d, =CH).

EXAMPLE 5

1-(β-D-2-Deoxygalactopyranosyl)-5-fluorouracil and 1-(α-D-2-Deoxygalactopyranosyl)-5-fluorouracil

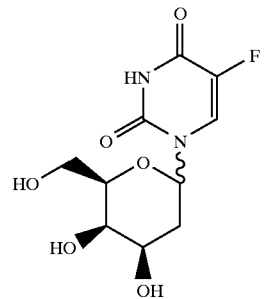

The above compound was prepared using the method described in Example 1, using peracetylated 2-deoxygalactose as the starting material. This gave a colourless product (95% yield for the second step).

The product was obtained as a mixture of the α and β anomers. These may be separated by the usual methods, for example, HPLC, column chromatography.

Mp. 105–109° C.

Anal. Calc. for $C_{10}H_{13}FN_2O_6$ Requires C 43.48 H 4.74 N 10.14 Found C 43.13 H 4.90 N 9.60

$^1$H NMR (β-anomer): δ1.98–2.13 (2H, m, CH), 3.83 (3H, m, CH, $CH_2$), 3.94 (1H, m, CH), 4.11 (1H, m, CH), 5.81 (1H, dd, CH), 8.12 (1H, d, =CH).

$^1$H NMR (α-anomer): δ1.98–2.2 (2H, m, CH), 3.8–3.9 (2H, m, CH), 3.95–4.0 (1H, m, CH), 4.15 (1H, m, CH), 4.6 (1H, m, CH), 6.30–6.35 (1H, dd, CH), 8.2 (1H, d, =CH).

EXAMPLE 6

1-(β-L-2-Arabinopyranosyl)-5-fluorouracil and 1-(α-L-2-Arabinopyranosyl)-5-fluorouracil

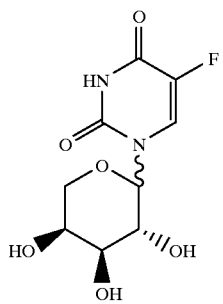

The above compound was prepared using the method described in Example 1, using peracetylated L-arabinose as the starting material. This gave a colourless product (68% yield for the second step). The product was obtained as a mixture of the α and β anomers. These may be separated by the usual methods, for example, HPLC, column chromatography.

Mp. 185–190° C.

Anal. Calc. for $C_9H_{11}FN_2O_6$ (+0.5$H_2O$) Requires C 39.85 H 4.43 N 10.33 Found C 39.67 H 4.48 N 9.86

$^1$H NMR (β): δ3.85–4.0 (4H, m, CH, $CH_2$), 4.05–4.15 (1H, m, CH), 4.4–4.45 (1H, m, CH), 5.55 (1H, d, CH), 8.05–8.1 (1H, d, =CH).

$^1$H NMR (α): δ3.8 (4H, m, CH, $CH_2$), 4.05–4.15 (1H, m, CH), 4.2–4.25 (1H, m, CH), 5.9 (1H, d, CH), 8.0–8.02 (1H, d, =CH).

EXAMPLE 7

1-(β-D-2-O-Acetylgalactopyranosyl)-5-fluorouracil

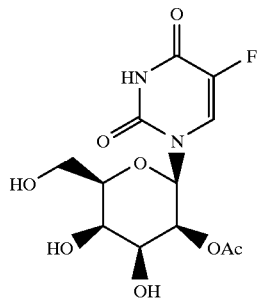

A mixture of 1-β-D-galactopyranosyl-5-fluorouracil (0.38 g, 1.30 mmol) and triphenylmethyl chloride (0.54 g, 1.95 mmol) was stirred in pyridine (5 ml) at room temperature for 2 h. The reaction mixture was co-evaporated under reduced pressure with toluene (×3) and the crude product purified by flash chromatography (20:1–10:1 DCM/MeOH) to give pure 1-(β-D-6-O-tritylgalactopyranosyl)-5-fluorouracil.

The above product (0.14 g, 0.26 mmol) and p-toluenesulphonic acid (0.065 g, cat.) were stirred in a mixture of 2,2-dimethoxypropane (5 ml) and acetone (5 ml) at room temperature overnight. The reaction was neutralised with triethylamine (10 drops) and evaporated under reduced pressure. The residue was purified by flash chromatography (50:1 DCM/MeOH) to give 1-(β-D-3,4-isopropylidene-6-O-tritylgalactopyranosyl)- 5-fluorouracil.

The above isopropylidene product (0.092 g, 0.16 mmol) was stirred in a mixture of pyridine (4 ml) and acetic anhydride (4 ml) at room temperature fro 2 h. The reaction was co-evaporated under reduced pressure with toluene (×3) and the product 1-(β-D-2-O-acetyl-3,4-isopropylidyl-6-O-tritylgalactopyranosyl)-5-fluorouracil used in the next step without further purification.

The above product (0.13 g, 0.21 mmol) was heated in acetic acid (70%, 10 ml) at 70–80° C., overnight. The reaction mixture was co-evaporated under reduced pressure with toluene (×3) and purified by flash chromatography (15:1 DCM/MeOH) to give the desired product.

$^1$H NMR (DMSO): δ1.90 (3H, s, $CH_3$), 3.49 (3H, m, CH, CH2), 3.71 (2H, m, CH), 3.79 (1H, m, CH), 4.60–4.71 (2H, s, OH), 5.02 (1H, dd, CH), 5.10–5.18 (1H, s, OH), 5.52 (1H, dd, CH), 8.08 (1H, d, CH).

EXAMPLE 8

1-(β-D-2,6-Di-O-Acetylgalactopyranosyl)-5-fluorouracil

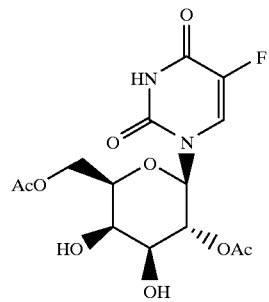

A mixture of 1-β-D-galactopyranosyl-5-fluorouracil (0.10 g, 0.34 mmol), imadazole (0.026 g, 0.38 mol) and tert-butylchlorodiphenylsilane (0.1 ml, 0.38 mmol) was stirred in DMF (2 ml) at room temperature for 18 h. The reaction mixture was co-evaporated under reduced pressure with toluene (×3) and purified by flash chromatography (15:1-8:1 DCM/MeOH) to give 1-β-D-6-O-tert-butyldiphenyl silyl-galactopyranosyl-5-fluorouracil.

The above silyl ether product (0.16 g, 0.3 mmol) and pyridinium p-toluenesulphonate (0.078 g, 0.30 mmol) was stirred at room temperature in a mixture of acetone (2 ml) and 2,2-dimethoxy propane (2 ml) for 30 min. The reaction mixture was then heated to 80° C. for 36 h. After cooling to room temperature the reaction was evaporated under reduced pressure and the purified by flash chromatography (30:1 DCM/MeOH) to give 1-β-D-3,4-isopropylidyl-6-O-tert-butyldiphenylsilyl-galactopyranosyl-5-fluorouracil.

The above isopropylidene product (0.13 g, 0.25 mmol) was stirred in a mixture of pyridine (2 ml) and acetic anhydride (2 ml) at room temperature for 2 h. The reaction mixture was co-evaporated under reduced pressure with toluene (×3) and purified by flash chromatography (100:1-80:1 DCM MeOH) to give 1-β-D-2-O-acetyl-3,4-isopropylidyl-6-O-tert-butyldiphenylsilyl-galactopyranosyl-5-fluorouracil. The above product (0.12 g, 0.20 mmol) was treated with tetrabutylammonium fluoride (1.1M solution in THF; 0.2 ml, 0.20 mmol) in THF (2 ml) at room temperature for 16 h. The reaction mixture was evaporated under reduced pressure and purified by flash chromatography (25:1 DCM/MeOH) to give 1-β-D-2-O-acetyl-3,4-isopropylidyl-galactopyranosyl-5-fluorouracil.

The product isopropylidene (0.07 g, 0.19 mmol) was stirred in a mixture of pyridine (2 ml) and acetic anhydride (2 ml) at room temperature for 1.5 h. The reaction mixture was co-evaporated under reduced pressure with toluene (×3) and purified by flash chromatography (100:1 DCM/MeOH) to give 1-β-D-2,6-di-O-acetyl-3,4-isopropylidyl-galactopyranosyl-5-fluorouracil.

Finally, the above product (0.06 g, 0.14 mmol) was treated with acetic acid (70%; 10 ml) at 80° C. for 18 h. After co-evaporation under reduced pressure with toluene (×3) the desired product was purified by flash chromatography (30:1-20:1 DCM/MeOH) to give the desired product (0.031 g, 57%).

$^1$H NMR (DMSO): δ2.01 (3H, s, CH3), 2.08 (3H, s, CH3) 3.35 (1H, m, OH), 3.78 (1H, m, CH), 3.91 (1H, m, CH), 4.18 (2H, m, CH2), 4.24 (1H, m, CH), 5.02 (1H, dd, NH), 5.15 (1H, t, CH), 5.36 (1H, d, OH), 5.68 (1H, dd, CH), 8.10 (1H, d, CH).

EXAMPLE 9

1-(β-D-2-Deoxy-2-N-acetyl-6-O-acetylgalactopyranosyl)-5-fluorcuracil

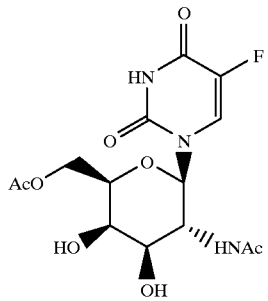

A mixture of 1-(β-D-2-Deoxy-2-N-acetylgalactopyranosyl)-5-fluorouracil (0.085 g, 0.26 mmol), imadazole (0.019 g, 0.28 mmol) and tert-butylchlorodiphenylsilane (0.073 g, 0.28 mmol) was stirred in DMF (2 ml) at 80° C. for 12 days. The reaction mixture was cooled, co-evaporated under reduced pressure with toluene (×3) and purified by flash chromatography (20:1-10:1 DCM/MeOH) to give 1-(β-D-2-Deoxy-2-N-acetyl-6-O-tert-butyldiphenylsilyl galactopyranosyl)-5-fluorouracil.

The above silyl ether product (0.1 g, 0.18 mmol) and pyridinium p-toluenesulphonate (0.044 g, 0.18 mmol) was stirred at room temperature in a mixture of acetone (3 ml) and 2,2-dimethoxy propane (3 ml) for 30 min. The reaction mixture was then heated to 70° C. for 17 h. After cooling to room temperature the reaction was evaporated under reduced pressure and the purified by flash chromatography (30:1-25:1 DCM/MeOH) to give 1-(β-D-2-Deoxy-2-N-acetyl-3,4-isopropylidyl-6-O-tert-butyldiphenylsilyl galactopyranosyl)-5-fluorouracil.

The above product (0.057 g, 0.09 mmol) was treated with tetrabutylammonium fluoride (1.1M solution in THF; 0.1 ml, 0.11 mmol) in THF (2 ml) at room temperature for 17 h. The reaction mixture was evaporated under reduced pressure and purified by flash chromatography (10:1-5:1 DCM/MeOH) to give 1-(β-D-2-Deoxy-2-N-acetyl-3,4-isopropylidylgalactopyranosyl)-5-fluorouracil.

The product isopropylidene (0.028 g, 0.08 mmol) was stirred in a mixture of pyridine (1 ml) and acetic anhydride (1 ml) at room temperature for 1 h. The reaction mixture was co-evaporated under reduced pressure with toluene (×3) and purified by flash chromatography (60:1 DCM/MeOH) to give 1-(β-D-2-Deoxy-2-N-acetyl-6-O-acetyl-3,4-isopropylidyl galactopyranosyl)-5-fluorouracil.

Finally, the above product (0.024 g, 0.06 mmol) was treated with acetic acid (70%; 10 ml) at 70° C. for 2 days. After co-evaporation under reduced pressure with toluene (×3) the desired product was purified by flash chromatography (20:1-10:1 DCM/MeOH) to give the desired product (0.010 g, 46%).

$^1$H NMR (DMSO): δ1.77 (3H, S, CH3), 2.04 (3H, s, CH3), 3.41 (2H, m, OH, CH), 3.74 (2H, m, OH, CH), 3.92 (1H, m, CH), 4.14 (2H, m, CH), 4.98 (1H, s, NH), 5.41 (1H, dd, CH), 7.89 (1H, dd, NH), 8.11 (1H, dd, CH).

EXAMPLE 10

1-(β-D-2-Deoxy-2-N-acetylgalactopyranosyl)-5-fluorouracil

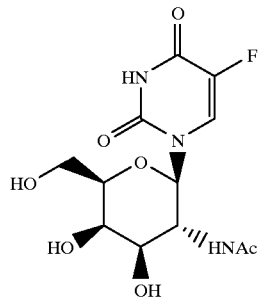

The above compound was prepared using the method described in Example 1, using peracetylated D-2-deoxy-2-N-acetylgalactose as the starting material.

$^1$H NMR (D$_2$O) δ2.0 (3H, s, CH3), 3.82–3.9 (2H, m, CH), 3.92–4.02 (2H, m, CH), 4.1 (1H, d, CH), 4.2–4.25 (1H, dd, CH), 5.7 (1H, dd, CH), 8.05 (1H, d, =CH).

EXAMPLE 11

1-β-D-Galactoyranosyl-5-fluorocytosine

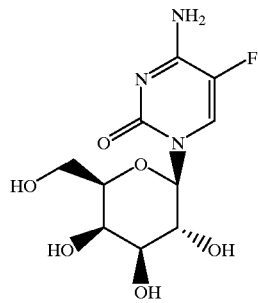

The above compound was prepared using the method described in Example 1, using peracetylated galactose and flucytosine as the starting materials. This gave a colourless product (55% yield for the second step).

Mp. 170–175° C.

Anal. Calc. for C$_{10}$H$_{14}$FN$_3$O$_6$ (+H$_2$O) Requires C 38.83 H 5.17 N 13.59 Found C 39.21 H 5.14 N 13.25

$^1$H NMR: δ3.8 (2H, m, CH), 3.85–4.0 (3H, m, CH, CH$_2$), 4.08 (1H, s, CH), 5.65 (1H, d, CH), 8.0 (1H, d, =CH).

EXAMPLE 12

1-(β-D-2-Deoxyglucopyranosyl)-5-fluorocytosine and 1-(α-D-2-Deoxyglucopyranosyl)-5-fluorocytosine

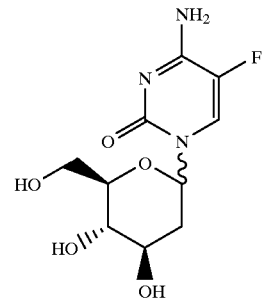

The above compound was prepared using the method described in Example 1, using peracetylated 2-deoxyglucose and flucytosine as the starting materials. This gave a colourless product (85% yield for the second step).

The product was obtained as a mixture of the α and β anomers. These may be separated by the usual methods, for example, HPLC, column chromatography.

Mp. 105–109° C.

Anal. Calc. for C$_{10}$H$_{14}$FN$_3$O$_5$ (+H$_2$O) Requires C 40.95 H 5.46 N 14.33 Found C 42.15 H 5.35 N 14.20

$^1$H NMR (β-anomer): δ2.15–2.19 (1H, m, CH), 2.39–2.43 (1H, m, CH), 3.32 (1H, m, CH), 3.78–3.89 (2H, m, CH$_2$), 4.08 (1H, m, CH), 4.18 (1H, m, CH), 6.13 (1H, dd, CH), 8.0 (1H, m, =CH)

$^1$H NMR (α-anomer): δ1.95–2.05 (1H, m, CH), 2.2–2.35 (1H, m, CH), 3.45–3.55 (1H, m, CH), 3.6–3.75 (2H, m, CH), 3.85–3.95 (1H, m, CH), 4.0–4.05 (1H, m, CH), 5.95–6.0 (1H, m, CH), 7.95 (1H, d, =CH).

EXAMPLE 13

1-α-D-Mannopyranosyl-5-fluorocytosine

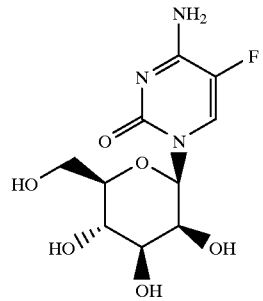

The above compound was prepared using the method described in Example 1, using peracetylated mannose and flucytosine as the starting materials. This gave a colourless crystaline product (75% yield for the second step).

Mp. 145–150° C.

Anal. Calc. for C$_{10}$H$_{14}$FN$_3$O$_6$ (+H$_2$O) Requires C 38.83 H 5.17 N 13.59 Found C 39.17 H 5.10 N 13.55

$^1$H NMR: δ3.75–3.78 (1H, dd, CH), 3.98 (1H, s, CH), 4.1 (1H, m, CH), 4.2–4.3 (3H, m, CH, CH$_2$), 6.05–6.1 (1H, d, CH), 8.0 (1H, d, =CH).

EXAMPLE 14

1-(β-D-2-Deoxy-2-N-acetylgalactopyranosyl)-5-fluorocytosine

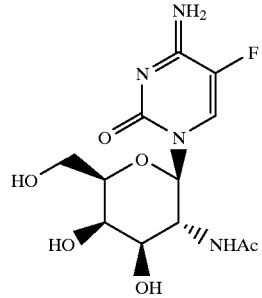

The above compound was prepared using the method described in Example 1, using peracetylated D-2-deoxy-2-N-acetylgalactose and 5-fluorocytosine as the starting materials.

$^1$H NMR (D$_2$O): δ2.21 (3H, s, CH3), 3.79 (2H, m, CH2), 3.91 (2H, m, CH, CH), 4.08 (1H, d, CH), 4.15 (1H, m, CH), 5.63 (1H, dd, CH), 8.00 (1H, d, CH).

EXAMPLE 15

1-(β-D-2-Deoxygalactopyranosyl)-5-fluorocytosine and 1-(α-D-2-Deoxygalactopyranosyl)-5-fluorocytosine

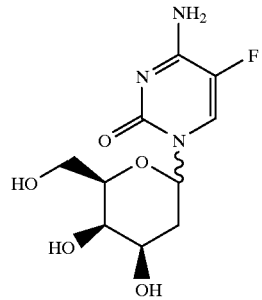

The above compound was prepared using the method described in Example 1, using peracetylated D-2-deoxygalactose and 5-fluorocytosine as the starting materials.

The product was obtained as a mixture of the α and β anomers. These may be separated by the usual methods, for example, HPLC, column chromatography.

3H NMR (D$_2$O β-product): δ1.81 (1H, m, CH), 1.95 (1H, m, CH), 3.68 (3H, m, CH2, CH), 3.80 (1H, d, CH), 3.95 (1H, m, CH) , 5.62 (1H, dd, CH) , 7.90 (1H, d, CH)

$^1$H NMR (D$_2$O α-product): δ2.13 (2H, m, CH2), 3.62 (1H, dd, CH), 3.77 (1H, m, CH), 3.90 (2H, m, CH2), 4.18 (1H, m, CH), 6.00 (1H, d, CH), 7.81 (1H, d, CH).

EXAMPLE 16

1-β-L-Arabinopyranosyl-5-fluorocytosine

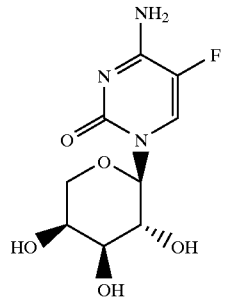

The above compound was prepared using the method described in Example 1, using peracetylated L-arabinose and 5-fluorocytosine as the starting materials.

$^1$H NMR (D$_2$O): δ3.78 (3H, m, CH2, CH) , 3.94 (2H, m, CH, CH), 5.42 (1H, dd, CH), 7.83 (1H, d, CH).

EXAMPLE 17

1-α-D-Lyxopyranosyl-5-fluorocytosine

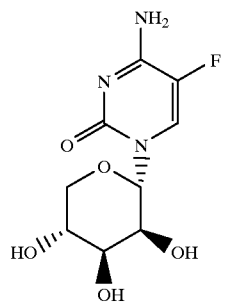

The above compound was prepared using the method described in Example 1, using peracetylated D-Lyxose and 5-fluorocytosine as the starting materials.

$^1$H NMR (D$_2$O): δ3.95 (2H, m, CH2), 4.18 (2H, m, CH, CH), 4.25 (1H, t, CH), 5.91 (1H, dd, CH), 8.00 (1H, d, CH).

EXAMPLE 18

1-β-D-Arabinopyranosyl-5-fluorocytosine

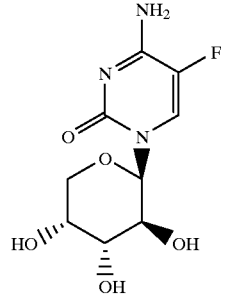

The above compound was prepared using the method described in Example 1, using peracetylated D-arabinose as the starting material.

$^1$H NMR (D$_2$O): δ3.77 (3H, m, CH2, CH), 3.92 (2H, m, CH), 5.42 (1H, dd, CH), 7.84 (1H, d, CH).

EXAMPLE 19

Toxicity

The toxicity of Compound 1 (as described in Example 1) relative to 5-FU was determined in nude mice. Clinical grade 5-FU was used to provide a point of comparison with other toxicity studies in the literature. Animals were injected six times ip, in groups of 5, every 48 hours, with various doses of 5-FU or Compound 1.

TABLE 1

Single bolus toxicity of 5FU and Compound 1

|  | LD10# | LD50# |
|---|---|---|
| 5-FU | 165 mg/kg | 360 mg/kg |
|  | MAD* |  |
| Compound 1 | 1300 mg/kg |  |

NCI data base
* MAD: maximal achievable dose

EXAMPLE 20

Efficacy In Vivo

Nude mice were inoculated with subcutaneous human HepG2 flank tumours to determine the antitumour activity of Compound 1 in vivo. After allowing the tumours to develop for the first seven days, we attempted to prevent tumour progression by seven ip treatments every 48 hours at doses of 1300 mg/kg. Compounds 1, 6, 2 and 10 (as described in Examples 1, 6, 2 and 10) significantly slowed the rate by which the disease progressed in treated animals, while they still kept a very healthy appearance. This led to an increased survival time of treated mice over untreated animals, without causing any toxic side effects to the animals (Tables 2 and 3).

TABLE 2

Number of mice surviving after tumour innoculation

| Days after Tumour Innoculation | 0 | 17 | 25 | 30 |
|---|---|---|---|---|
| Control | 5 | 3 | 3 | 0 |
| 5-FU | 5 | 3 | 2 | 0 |
| Compound 1 | 5 | 3 | 2 | 1 |
| Compound 6 | 5 | 4 | 2 | 2 |
| Compound 2 | 5 | 5 | 3 | 2 |
| Compound 10 | 5 | 3 | 2 | 1 |

TABLE 3

Average tumour size (at sacrifice)

| Control | 5-FU | Compound 1 | Compound 6 | Compound 2 | Compound 10 |
|---|---|---|---|---|---|
| 10.4 | 10.2 | 9.4 | 6.2 | 5.6 | 9 |

I claim:
1. A compound of the formula (I):

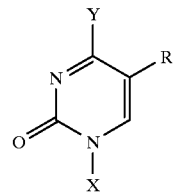

wherein:
R is fluoro;
Y is OH;
X is:

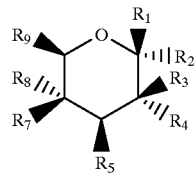

wherein:
R$_1$ is a bond and R$_2$ is hydrogen;
R$_3$ is hydrogen and R$_4$ is OH, OAc or NHAc;
R$_5$ is OH;
R$_8$ is hydrogen and R$_7$ is OH; and
R$_9$ is CH$_2$OH or CH$_2$OAc;
and enantiomers thereof.
2. The compound of claim 1, which is the D enantiomer.
3. The compound of claim 2, which is
1-β-D-Galactopyranosyl-5-fluorouracil;
1-(β-D-2-deoxy-N-Acetylgalactosaminopyranosyl)-5-fluorouracil;
1-(β-D-2-O-Acetylgalactopyranosyl)-5-fluorouracil;
1-(β-D-2-deoxy-2-N-Acetyl-6-O-acetylgalactosaminopyranosyl)-5-fluorouracil; or
1-(β-D-2,6-Di-O-Acetylgalactopyranosyl)-5-fluorouracil.
4. The compound of claim 2 which is
1-β-D-Galactopyranosyl-5-fluorouracil.
5. A pharmaceutical composition comprising a therapeutically effective amount of the compound of claims 1, 2, 3 or 4 and a pharmaceutically acceptable carrier.
6. The pharmaceutical composition of claim 5, which is suitable for oral administration.
7. A method for treatment of cancer which comprises the step of administering to a patient in need of such treatment an effective amount of the compound of claims 1, 2, 3 or 4.
8. The method of claim 7, wherein the cancer is liver cancer.
9. The method of claim 8, wherein the compound is administered orally.
10. A method for prophylaxis or treatment of metastatic liver cancer which comprises the step of administering to a patient in need of such treatment an effective amount of the compound of claim 1 or 4.
11. The method of claim 10, wherein the compound is administered orally.
12. A method for treatment of hepatoma which comprises the step of administering to a patient in need of such treatment an effective amount of the compound of claim 1 or 4.

13. The method of claim 12, wherein the compound is administered orally.

14. A method of inhibiting cell division which comprises administering to a patient in need of such inhibition an effective amount of the compound of claim 1.

15. A compound of the formula (I):

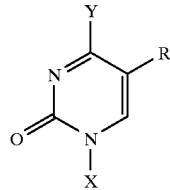

wherein:
R is fluoro;
Y is NH₂;
X is:

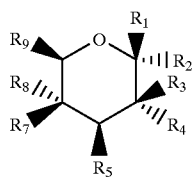

wherein: R₁ is a bond and R₂ is hydrogen;
either R₃ or R₄ is hydrogen, with the other being hydrogen, OH, OAc or NHAc;
R₅ is OH or OAc;
R₇ is OH or Oac and R₈ is hydrogen; and
R₉ is CH₂OH or CH₂OAc;
and enantiomers thereof.

16. The compound of claim 15, which is
1-β-D-Galactopyranosyl-5-fluorocytosine;
1-(β-D-2-Deoxy-2-N-acetylgalactopyranosyl)-5-fluorocytosine; or
1-(β-D-2-Deoxygalactopyranosyl)-5-fluorocytosine.

17. A pharmaceutical composition comprising a therapeutically effective amount of the compound of claim 15 or 16 and a pharmaceutically acceptable carrier.

18. The pharmaceutical composition of claim 17, which is suitable for oral administration.

19. A method for treatment of a fungal infection, which comprises the step of administering to a patient in need of such treatment an effective amount of the compound of claim 15.

20. A compound of the formula (I):

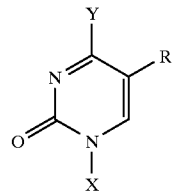

wherein:
R is fluoro;
Y is OH;
X is:

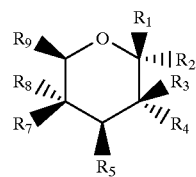

wherein:
R₁ is a bond and R₂ is hydrogen;
R₃ is hydrogen and R₄ is OAc;
R₅ is OAc
R₇ is OAc and R₈ is hydrogen; and
R₉ is CH₂OAc.

* * * * *